United States Patent [19]
Pyun et al.

[11] Patent Number: 6,162,437
[45] Date of Patent: Dec. 19, 2000

[54] **METHOD FOR INHIBITING INTERLEUKIN-6 PRODUCTION BY ADMINISTERING EXTRACTS FROM ROOT OF *STEPHANIA TETRANDRA***

[75] Inventors: Kwang-Ho Pyun, Seoul; Inpyo Choi, Taejon; Hyung-Sik Kang, Taejon; Jung-Joon Lee, Taejon; Young-Ho Kim, Taejon, all of Rep. of Korea

[73] Assignee: Korea Institute of Science & Technology, Seoul, Rep. of Korea

[21] Appl. No.: 08/978,321

[22] Filed: Nov. 25, 1997

Related U.S. Application Data

[63] Continuation-in-part of application No. 08/750,462, filed as application No. PCT/KR95/00073, Dec. 5, 1995, abandoned.

[51] Int. Cl.[7] ................................................ A61K 35/78
[52] U.S. Cl. ........................ 424/195.1; 424/838; 514/783
[58] Field of Search ......................... 514/783; 424/195.1, 424/838

[56] References Cited

FOREIGN PATENT DOCUMENTS 9533473  12/1995  WIPO.

OTHER PUBLICATIONS

EJ Kovacs, Fibrogenic cytokines: the role of immune mediators in the development of scar tissue; Immunology Today, vol. 12, No. 1 1991, pp. 17–23.

Suppression of Interleukin–1 and Tumor Necrosis Factor–α Production by Acanthoic Acid, (–)–Pimara–9 (11), 15–dien–19–oic Acid, and its Antifibroic Effects in Vivo, 1996, Academic Press, Inc. Cellular Imunology 170, 212–221 (1996) Article No. 0154.

Xiufen et al., Ecotoxicology & Environmental Safety 7:306, 1983.

Quanlu et al, Chinese J. of Tubercular and Respiratory Diseases 4:321–323, 1981. English translation provided.

Kang Cellular Immunology 170:212 1996.

Seow, Int Archs Allergy appl Immun. 85:410, 1988.

Kang, Mediators of Inflammation 5:280, 1996.

Ferrante Clin exp Immunol 80:232, 1990.

Seow, Clin exp. Immunol 75:47,1989.

Fundamental in Immunology, W. Paul, ed. 1980 pp. 646–647, Rasen Press, NY.

*Primary Examiner*—Nancy A. Johnson
*Attorney, Agent, or Firm*—Anderson Kill & Olick, PC

[57] ABSTRACT

Method for inhibiting the production of interleukin-6 (hereinafter, referred to as "IL-6") in human body, which comprises administering extracts from a root of *Stephania tetrandra* S. Moore; and method for treating a patient of an immune disease caused by an overproduction of interleukin-6 by inhibiting the production of interleukin-6, which comprises administering extracts from a root of *Stephania tetrandra* S. Moore to the patient.

1 Claim, 18 Drawing Sheets

SEQUENCE LISTING (1) GENERAL INFORMATION:

(iii) NUMBER OF SEQUENCES: 3

(2) INFORMATION FOR SEQ ID NO: 1:

```
        (i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 1:

CGCCGGCGTT TTTTTTTTTT TTTTTT                                               26

(2) INFORMATION FOR SEQ ID NO: 2:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 2:

ATGAACTCCT TCTCCACAAG CGC                                                  23

(2) INFORMATION FOR SEQ ID NO: 3:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 3:

GAAGAGCCCT CAGGCTGGAC TG                                                   22
```

METHOD FOR INHIBITING INTERLEUKIN-6 PRODUCTION BY ADMINISTERING EXTRACTS FROM ROOT OF *STEPHANIA TETRANDRA*

CROSS REFERENCE TO RELATED APPLICATION

This application is a continuation-in-part application of U.S. Ser. No. 08/750,462 filed on Dec. 6, 1996, now abandoned, which is a 371 of PCT/KR95/00073 filed Dec. 5, 1995.

FIELD OF THE INVENTION

The present invention relates to a method for inhibiting the production of interleukin-6 (hereinafter, referred to as "IL-6") in human body, which comprises administering extracts from a root of *Stephania tetrandra* S. Moore; and a method for treating a patient of an immune disease caused by an overproduction of interleukin-6 by inhibiting the production of interleukin-6, which comprises administering extracts from a root of *Stephania tetrandra* S. Moore to the patient.

BACKGROUND OF THE INVENTION

*Stephania japonica* Miers and *Sinomenium acutum* Rehd et Wile(Menispermaceae), which are found in southern parts and Cheju island in the Republic of Korea, have been used for long time as an analgesic and anti-inflammatory agent. On the other hand, *S. tetrandra* S. Moore(Menispermaceae), which is not found in the Republic of Korea, has been used traditionally as remedies for neuralgia and arthritis in, e.g., China. Especially, the alkaloid tetrandrine has been used as, e.g., an anti-inflammatory and anti-hypertensive agent. *S. tetrandra* S. Moore has been reported to have anti-phagocytic and anti-oxidizing effects (Seow, W. K., et al., *Int. Archs. Allergy Appl. Immun.*, 85, 404(1988)), and to exhibit effectiveness in clinical and experimental silicosis models (Li, Q., et al., *Chinese J. Tuberc. Resp. Dis.*, 4, 321(1981); Xu, X., et al., *Ecotoxicol. Environ. Safety*, 7, 306(1983); and Liu, B., et al., *Ecotoxicol. Environ. Safety*, 7, 323(1983)), and is known to have the ability to inhibit the production of interleukin-1 and tumor necrosis factor-a which are secreted by human monocytes (Seow, W. K., et al., *Clin. Exp. Immunol.*, 75, 47(1989); and Ferrante, A., et al., *Clin. Exp. Immunol.*, 80, 232(1990)). Tetrandrine and its derivatives are reported to promote the function of brain (Tsumura & CO, WPI Acc. No.: 92-231935 (1992)) and have been developed as an antimalarial drug and also a stimulant for hair growth (Sunstar KK, WPI Acc. No.: 89-117236(1989)).

As is well known, IL-6 is a regulatory factor which participates in the growth, differentiation and activation of cells. It is produced and secreted by various organ cells, and plays an important role in defensive mechanisms of a human body (Hirano, T., et al., *Immunol. Today*, 11, 443(1990)).

IL-6, first discovered in a culture of monocytes, has been reported to induce the production of antibodies by B cells (Muraguchi, A., et al., *J. Immunol.*, 127, 412(1981)). Since the successful cloning of the cDNA of IL-6 by Hirano, T., et al. (*Nature*, 324, 73(1986)), IL-6 has been reported to serve as a growth factor for B cell hybridome and plasmocytoma (Snick, V. J., et al., *Proc. Natl. Acad. Sci. U.S.A.*, 83, 9679(1986)), and as a factor participating in hematopoiesis (Koike, K., et al., *J. Exp. Med.*, 168, 879(1988)). Further, IL-6 has been reported to have the functions of: stimulating the activation and growth of T cells (Lotz, M., et al., *J. Exp. Med.*, 167, 1253(1988)); inducing the acute phase response of liver cells (Geiger, T., et al., *Eur. J. Immunol.*, 18, 717(1988)); regulating cell differentiation in nerve system (Satoh, T., *Mol. Cell. Biol.*, 8, 3546(1988)); stimulating the growth of keratinocytes; regulating a bone metabolism; stimulating the growth of kidney mesangial cells; inhibiting the growth of melanoma and breast cancer cells, etc.

As has been reported, various diseases may result from an improper regulation of IL-6 production. Examples of the diseases reported are rheumatoid arthritis (Hirano, T., et al., *Eur. J. Immnol.*, 18, 1797(1988)), hepatocirrhosis (Deviere, J., et al., *Clin. Exp. Immunol.*, 77, 221(1989)), psoriasis (Grossman, R. M., et al., *Proc. Natl. Acad. Sci. U.S.A.*, 86, 6367(1989)), multiple myeloma (Bataille, R., et al., *J. Clin. Invest.*, 84, 2008(1989)), cardiac myxoma, AIDS (Miles, S. A., et al., *Proc. Natl. Acad. Sci. U.S.A.*, 87, 4068(1990)), and other autoimmune diseases. These observations have buttressed the importance of regulating the IL-6 production for the maintenance of the homeostasis of immune system in a human body and for the treatment and prophylaxis of diseases.

Accordingly, there have been proposed numerous approaches to regulate the production of interleukins. For instance, proliferation of myelocytes in a patient suffering from myeloma which is caused by an excessive secretion of IL-6 has been suppressed by employing antibodies against IL-6 or IL-6 receptor (Suzuki, H., *Eur. J. Immunol.*, 22, 1989(1992)). However, no substance or method has been reported to inhibit specifically the production of IL-6 and, therefore, there has still existed a need for the discovery of specific inhibitors against the production of IL-6.

SUMMARY OF THE INVENTION

Accordingly, it is an object of the present invention to provide a method for inhibiting the production of interleukin-6(hereinafter, referred to as "IL-6") in human body, which comprises administering extracts from a root of *Stephania tetrandra* S. Moore.

Another object of the present invention is to provide a method for treating a patient of an immune disease caused by an overproduction of interleukin-6 by inhibiting the production of interleukin-6, which comprises administering extracts from a root of *Stephania tetrandra* S. Moore to the patient.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
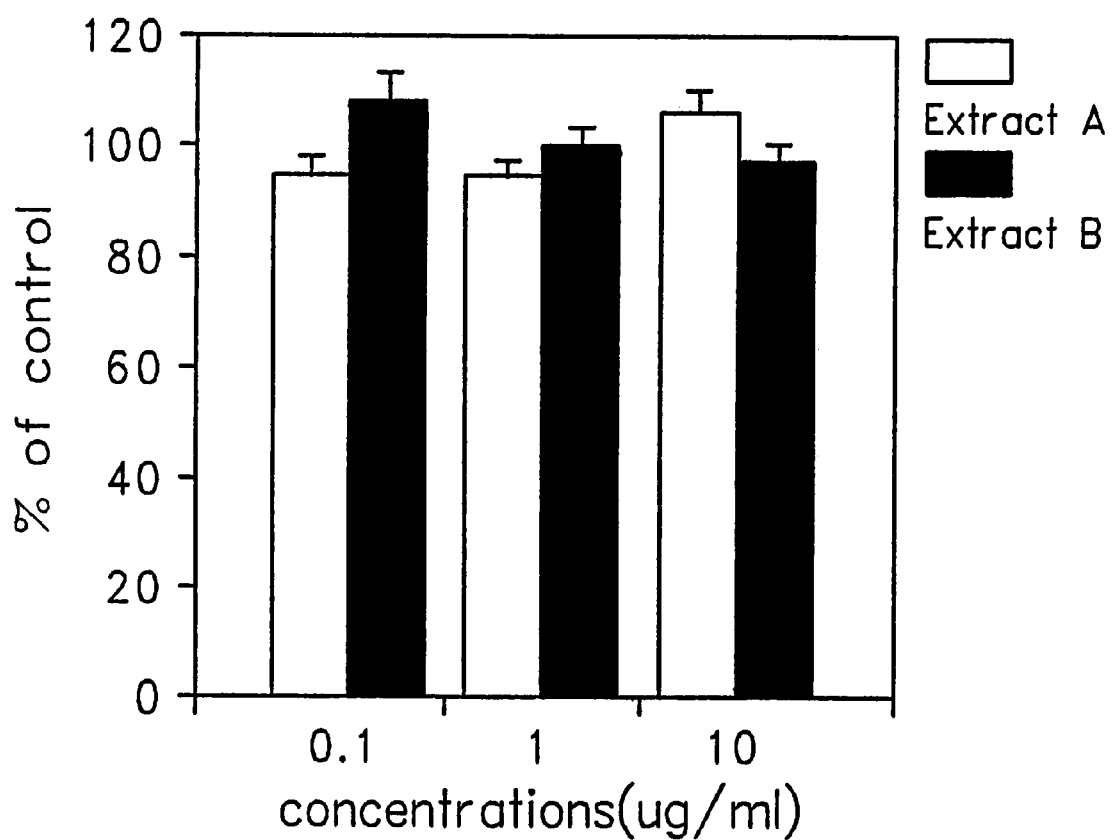
FIG. 1 shows the cytotoxicity of Extracts A and B of *S. tetrandra* S. Moore on human monocytes and macrophages.

All references cited herein are hereby incorporated in their entirety by reference.

In accordance with the present invention, it has been found that extracts from the root of *Stephania tetrandra* S. Moore possess the ability to specifically inhibit the production of IL-6; and therefore, are useful for the treatment of various immune diseases caused by an excessive production of IL-6.

Said extracts of *S. tetrandra* S. Moore may be prepared by employing various solvents, e.g., methanol, ethanol, hexane, $CH_2Cl_2$ or a mixture thereof, physiological saline, distilled water, etc. Especially, Extracts A, B, C and D of *S. tetrandra* S. Moore, which are further described below, may be prepared in accordance with the following preferred embodiment.

To 1 kg of dried root of *S. tetrandra* S. Moore is added 1 to 3l, preferably 2l of methanol; and the mixture is heated at a temperature ranging from 50 to 70° C. for a period ranging from 6 to 12 hours or at a room temperature for at least 24 hours, and filtered. Said procedure is repeated, preferably three times, and the combined filtrates are concentrated under a reduced pressure, e.g., 7 mmHg, to obtain Extract A.

100 g of said Extract A is partitioned with 200 to 400 ml, preferably 250 ml, of methanol and 200 to 400 ml, preferably 250 ml, of hexane. The methanol fraction is separated therefrom and then concentrated under a reduced pressure. The residue is adjusted to a pH ranging from 9 to 11 by employing ammonium hydroxide or sodium hydroxide. The resultant is partitioned with 400 to 800 ml, preferably 500 ml, of a mixture of distilled water and $CH_2Cl_2$(1:1 (v/v)). The $CH_2Cl_2$ fraction, i.e., alkaloid fraction, is separated therefrom and then concentrated under a reduced pressure to obtain Extract B.

On the other hand, 1 kg of dried root of *S. tetrandra* S. Moore is crushed, sieved and then suspended in distilled water or physiological saline in a concentration of 50 to 200 mg/ml, preferably 100 mg/ml. The resulting suspension is heated at a temperature ranging from 80 to 100° C., preferably 95° C., for 4 to 12 hours, preferably 6 hours. The heated suspension is filtered and the filtrate is concentrated under a reduced pressure to obtain Extract C.

In another process, 1 kg of dried root of *S. tetrandra* S. Moore is mixed with 1 to 3l, preferably 2l, of distilled water and heated at a temperature ranging from 80 to 100° C., preferably 95° C., for 4 to 15 hours, preferably 12 hours. The heated mixture is filtered and the filtrate is concentrated under a reduced pressure. The residue is stored at a temperature ranging from -70 to -90° C., preferably -80° C., for 2 to 10 hours, preferably 8 hours, and then lyophilized for 4 to 8 hours, preferably 6 hours, to obtain powdery Extract C.

Further, Extract D may be obtained by repeating, preferably three times, an extraction procedure which comprises adding 1 to 3l, preferably 2l, of ethanol to 1 kg of dried root of *S. tetrandra* S. Moore and heating the mixture at a temperature ranging from 60 to 90° C. for a period ranging from 6 to 12 hours or at a room temperature for more than 24 hours, filtering and concentrating the combined filtrates under a reduced pressure.

Each of said Extracts A, B, C and D exhibits an anti-inflammatory effect, inhibits the synthesis of collagen and the production of the reactive oxygen species and reduces GOT and GPT level in serum. Therefore, they can be employed alone or in combination with each other for the treatment of such immune diseases caused by an excessive production of IL-6 as rheumatoid arthritis, hepatocirrhosis, psoriasis, multiple myeloma, cardiac myxoma, silicosis, and AIDS. These immune diseases are characterized by collagen synthesis, production of reactive oxygen species, proliferation of synoviocytes, or increase in serum GOT and GPT levels. Preferably, however, extract A may be applied for the treatment of inflammatory disease, arthritis and fibrogenic disease; Extract B, for arthritis and autoimmune hepatocirrhosis; Extract C, for silicosis and fibrogenic disease of liver; and Extract D, for hepatocirrhosis.

A pharmaceutical composition, which is useful for the method of the present invention for inhibiting the production of interleukin-6 or for the method for the treatment of immune diseases caused by an excessive production of IL-6, may comprise pharmaceutically acceptable excipients, carriers or diluents in combination with an extract of *S. tetrandra* S. Moore as an active ingredient. The pharmaceutical formulations may be prepared in accordance with any of the conventional procedures.

In preparing the compositions, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the compositions may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

In order to inhibit the production of interleukin-6 in human body, or to treat a patient of an immune disease caused by an overproduction of interleukin-6 by inhibiting the production of interleukin-6, the pharmaceutical compositions can be administered by a variety of routes including oral, transdermal, subcutaneous, intravenous and intramuscular introduction. A typical daily dose of the active ingredient may range from about 1 to 500 pg/kg body weight, preferably 30 to 300 μg/kg body weight, and can be administered in a single dose or in divided doses. However, it should be understood that the amount of the active ingredient actually administered ought to be determined in light of various relevant factors including the condition to be treated, the chosen route of administration, the age and weight of the individual patient, and the severity of the patient's symptom; and, therefore, the above dose should not be intended to limit the scope of the invention in any way.

The following Preparation Example and Examples are intended to further illustrate the present invention without limiting its scope; and the experimental methods used in the Examples can be practiced in accordance with the Reference Examples given herein below, unless otherwise stated.

Further, percentages given below for solid in solid mixture, liquid in liquid, and solid in liquid are on a wt/wt, vol/vol and wt/vol basis, respectively, unless specifically indicated otherwise.

Preparation Example: Preparation of Extracts of *Stephania tetrandra* S. Moore

About 4.0 kg of well-dried root of *S. tetrandra* S. Moore was chopped and extracted with about 5l of methanol for 2 days. The extraction procedure was repeated three times and the combined extracts were concentrated under a reduced pressure to obtain about 224 g of the methanol extract (Extract A) in a yield of 5.6%.

200 g of Extract A was partitioned with 500 ml of 90% methanol and 500 ml of n-hexane. 90% Methanol layer was separated and concentrated under a reduced pressure to remove methanol. The residue was adjusted to pH 10 with 0.1M $NH_4OH$ and partitioned with 600 ml of distilled water:$CH_2Cl_2$(1:1(v/v)) mixture. The $CH_2Cl_2$ layer, i.e., alkaloid fraction was then separated and concentrated under a reduced pressure to obtain about 25 g of Extract B in a yield of 0.6%.

On the other hand, Extract C for use in a test for the treatment of silicosis was prepared as follows. 1 kg of dried root of *S. tetrandra* S. Moore was crushed into powder, sieved (60 mesh) and then suspended in distilled water in a concentration of 100 mg/ml. The resulting suspension was heated at 100° C. for 6 hours end filtered. The filtrate was concentrated under a reduced pressure to obtain 80 g of water extract of *S. tetrandra* S. Moore (Extract C) in a yield of 8%, which was then stored at −20° C.

For the purpose of preparing Extract C for use in a test for the treatment of hepatocirrhosis, 1113.5 g of dried root of *S. tetrandna* S. Moore was introduced in a 3l round-bottomed flask equipped with a cooling apparatus with 2l of distilled water, and the mixture was heated at 95° C. for 12 hours and then filtered. The filtrate was concentrated under a reduced pressure by employing a rotary vacuum evaporator (Buchi 451), freezed in a deep freezer (SANYO, Japan) at −84° C. for 3 hours, and then lyophilized for 4 hours by employing lyophilizer (EYELA, Japan) to obtain 56.55 g of powdery Extract C in a yield of 5.1%.

Further, 500 g of dried root of *S. tetrandra* S. Moore was extracted with about 1.5l of ethanol at a room temperature for 3 days. The extraction procedure was repeated three times and the combined extracts was concentrated under a reduced pressure to obtain 13 g of ethanol extract of *S. tetrandra* S. Moore in a yield of 2.6%.

Reference Example 1

Separation of Cells for Assay (1) Separation of human monocytes, macrophages and neutrophils Normal human peripheral blood was heparin-treated and diluted with equal amount of Hank's balanced salt solution (HBSS: $Ca^{2+}$ and $Mg^{2+}$ free). The diluted blood was put into a centrifuge tube containing therein Ficoll-Hypaque (Sigma, St. Louis, Mo., U.S.A.) layer having a density of 1.077 piled up on Ficoll-Hypaque layer having a density of 1.119, and then centrifuged at 700xg for 30 minutes to obtain monocytes from the layer between Ficoll-Hypaque layer having a density of 1.077 and serum layer, and neutrophils from the layer between Ficoll-Hypaque layer having a density of 1.077 and that having a density of 1.119. The separated cells were washed twice with 4° C. HBSS($Ca^{2+}$ and $Mg^{2+}$ free) and suspended in RPMI 1640 medium (Gibco, Grand Island, N.Y., U.S.A.) containing 10% fetal bovine serum (FBS, Hyclone, Logan, Utah, U.S.A.). The suspensions were added to the wells of 24-well incubation plate (Costar, Cambridge, Mass., U.S.A.) and incubated at 37° C. for 2 hours to obtain monocytes, macrophages and neutrophils.

(2) Separation of fibroblasts

Fibroblasts were separated from rats by using a modification of the method of Phan, S. H., et al. described in *J. Clin. Invest.*, 76, 241(1985), as follows.

A rat was anesthetized with ether and its lungs were isolated on the aseptic worktable. The lungs were cut into small pieces in the size ranging from 2 to 4 mm and suspended in phosphate buffered saline(PBS) containing collagenase and 0.5% trypoin to digest the tissues at 37° C. for 2 hours. The suspension was filtered through sterilized gauze to remove, e.g., undigested tissues. The separated cells were washed with PBS two or three times and suspended into RPMI 1640 medium (Gibco, Grand Island, N.Y., U.S.A.) containing 10% fetal bovine serum (FBS, Hyclone, Logan, Utah, U.S.A.). The suspension was added to the wells of incubation plate and incubated at 37° C. for 1 to 2 days in 5% $CO_2$ incubator (Lunaire Environ, Inc., Pennsylvania, U.S.A.). The plate was washed with RPMI 1640 medium to remove the cells which did not adhere to the plate. Fresh medium was added to the plate and the incubation was continued until the confluent layer was formed. The cells undergone subcultures less than 5 times were used in the following tests.

NIH3T3 fibroblast (ATCC CRL 1658) was cultured in RPMI 1640 medium containing 10% FBS under the same conditions as described above.

(3) Separation of synoviocytes from rheumatoid arthritis patients

Synovial membrane tissue of a patient suffering from rheumatoid arthritis was washed three times with cool PBS and cut into small pieces having a size of 2 mm with sterile scissors, which was then suspended in DMEM (Sigma, U.S.A.) containing collagenaae A (5 mg/ml, BM, Indianapolis, Ind., U.S.A.) and DNase type I (0.15 mg/ml, Sigma) and incubated at 37° C. for 2 hours in a 5% $CO_2$ incubator. Then 0.5% trypsin-0.2% EDTA were added thereto and the incubation was continued for 30 minutes. The digested tissue was washed twice with PBS and once with DMEM, and isolated cells were suspended in DMEM containing 10% FBS (DMEM-10% FBS) and incubated for one week.

Thereafter, synovial adherent cells were isolated with trypsin-EDTA, washed with DMEM and then suspended in DMEM-5% FBS in a concentration of $10^5$ cells/ml. The suspension was added to the wells of a 24-well culture plate in an amount of 1 ml/well and incubated at 37° C. for 24 hours. The resulting culture was stored at −20° C. to use in the next experiments, and a part of it was subcultured and stored in liquid nitrogen tank in a freezed state.

(4) Treatment of cells with extracts of *S. tetrandra* S. Moore

Extracts of *S. tetrandra* S. Moore were added in various concentrations to $5 \times 10^5$/ml of cells which were obtained in the above procedures, and the cells were precultured at 37° C. for 1 hour in 5% $CO_2$ incubator. Then, 1 ml each of silica (100 μg/ml) and RPMI 1640 medium containing 2% FBS were added thereto and the cells were cultured under the same conditions as above for 48 hours. The culture supernatant was collected and centrifuged at 1,500 rpm for 10 minutes to remove the cells and silica. The obtained supernatant was dialyzed against PBS and filtered by 0.2 μm filtration syringe and the filtrate was stored at −20° C.

Reference Example 2
Assay for Cytotoxicities of Extracts of *S. tetrandra* S. Moore The cytotoxicities of the extracts of *S. tetrandra* S. Moore were determined by the following procedures.

According to the procedures of Reference Example 1 (4), $5 \times 10^5$ cells/ml each of monocytes and macrophages obtained in Reference Example 1 (1) were treated with 0.1, 1 and 10 μg/ml each of Extracts A and B obtained in the Preparation Example and incubated under the same conditions. In accordance with the method of Alley, M. C., et al. described in *Cancer Res.*, 48, 589(1988), the culture was added to the wells of the incubation plate in an amount of 1 ml/well, and 0.5 mg of 3-4,5-dimethylthiazol-2,5-diphenyl-tetrazoliumbromide (MTT, Sigma) was added to each of the wells. After incubating at 37° C. for 4 hours, the culture was centrifuged to remove supernatant. 100 μl Each of acidified isopropanol (0.04N HCl in isopropanol) was added to the cells in each well to elute formazan produced by the living cells, and optical density (O.D.) was determined at 540 nm by using an ELISA reader (Titertek multiskan Mcc/340) (FIG. 1).

FIG. 1 shows the relative values of optical density of the sample with respect to the concentration of Extract A or B when the optical density of the control group which was not treated with Extract A or B is regarded as 100%. When the survival rate of monocyte and macrophage decreases due to the toxicity of extracts of *S. tetrandra* S. Moore, the production of formazan also decreases, which causes the optical density to decrease. The samples treated with Extract A show no significant difference from the control group until the concentration of Extract A reaches 10 μg/ml, and, the samples treated with Extract B show similar results. Therefore, it is confirmed that Extracts A and B have no cytotoxicities at the concentration lower than 10 μg/ml and, hereinafter, all the tests were carried out in this concentration range. Both Extracts A and B showed cytotoxicities at the concentration of 100 μg/ml.

On the other hand, the cytotoxicities of Extracts C and D was confirmed by using rats. 40 mg each of Extract C and D was administered orally to rats twice a week for 17 weeks and, as a result, no toxicity to rats (death, loss of weight, etc.) was shown.

EXAMPLE 1
Inhibition of IL-6 Production in Human Monocytes and Macrophages by Extracts of *S. tetrandra* S. Moore The monocytes/macrophages obtained in Reference Example 1 (1) were incubated with 0.1 to 10 μg/ml of Extract A or B for 1 hours and treated with 100 μg/ml of silica for 48 hours. The culture was centrifuged to obtain eupernatant, which was then dialyzed against PBS. The activity of IL-6 therein was determined by using IL-6 dependent B9 hybridoma cell line.

B9 cell line (Dr. Kishimoto, T., Osaka University, Japan) was cultured on RPMI 1640 medium containing 10% FBS with the addition of 2U/ml of recombinant human IL-6, and the cells were washed three times with serum-free medium. The cells were suspended in RPMI 1640 medium containing 10% FBS in a concentration of $5 \times 10^4$ cells/ml, and the suspension was added to the wells of a 96-well incubation plate in an amount of 100 μl/well. Then, the plate was incubated at 37° C. under 5% $CO_2$ for 68 hours. 0.5 μCi of $^3$H-thymidine was added to the wells in an amount of 50 μl/well and incubation was continued for 4 hours. When the incubation was completed, the cells were collected on the glass fiber filter by using multiple cell harvester (Inotech) and the amount of incorporated $^3$H-thymidine was determined by liquid scintillation counter (Beckman, Somerset, N.J., U.S.A.).

Figure 2:
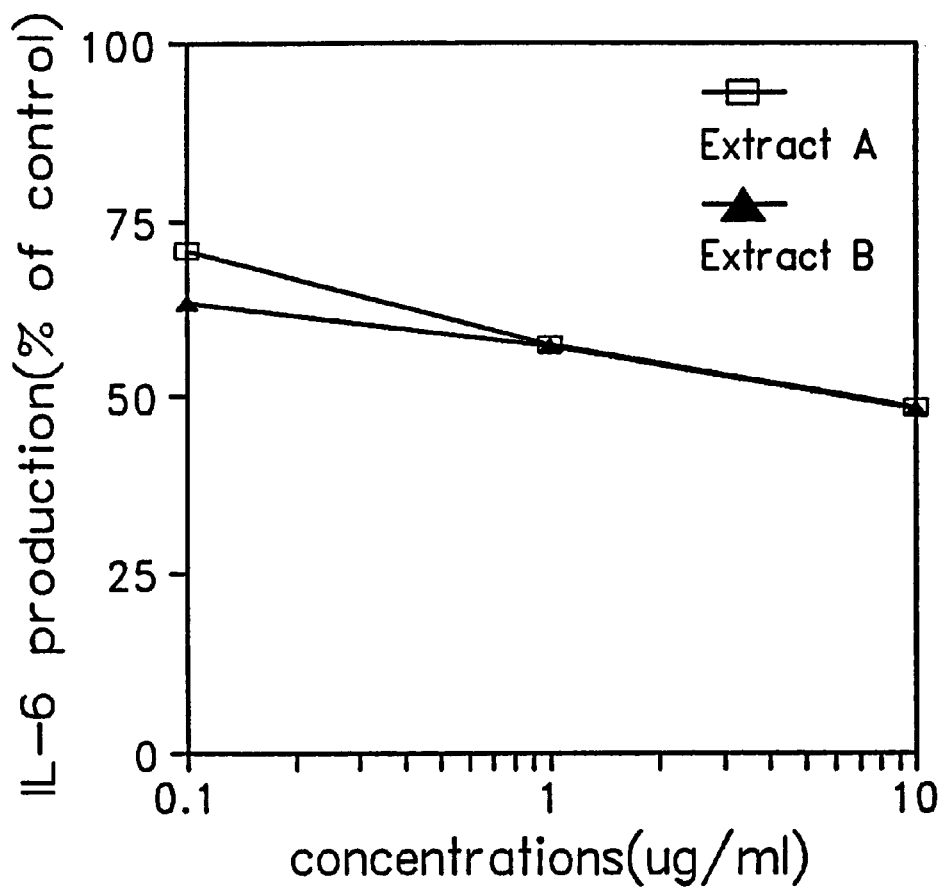
FIG. 2 depicts the inhibitory effect of Extracts A and B of *S. tetrandra* S. Moore on the production of IL-6 in human monocytes and macrophages.

FIG. 2 shows relative values of the amount of incorporated $^3$H-thymidine with respect to the concentration of Extract A or B when the amount of incorporated $^3$H-thymidine of the control group which was not treated with Extract A or B is regarded as 100%. As can be seen from FIG. 2, the production of IL-6 in monocyte/macrophage was inhibited by Extract A or B of *S. tetrandra* S. Moore in a concentration-dependent mode, and it was inhibited by 50% with 10 μg/ml of Extract A or B of *S. tetrandra* S. Moore.

EXAMPLE 2
Inhibition of IL-6 Production in Rat Alveolar Macrophage by Extracts of *S. tetrandra* S. Moore Rats were anesthetized with ketamine and their alveolar macrophage were obtained therefrom by inserting a sterilized thin tube into the branchia and repeating three times the injection and Bucking out of 10 ml of RPMI 1640 medium with a 30 ml syringe. The obtained cells were centrifuged at 400 xg for 5 minutes, suspended in 50 ml of RPMI 1640 medium containing 10% FBS and then incubated at 37° C. for 2 hours to adhere to the incubation plate. The plate was washed twice with PBS to remove alveolar lymphocytes (floating cells) and to obtain alveolar macrophages.

The alveolar macrophages were added to the wells of 24-well incubation plate in an amount of $2 \times 10^5$ cells/well and treated with 100 μg/ml of silica and 10 μg/ml of Extract A for 3 days. The culture was centrifuged to obtain supernatant, which was then dialyzed against PBS. The activity of IL-6 therein was determined by employing IL-6 dependent B9 hybridoma cell line in accordance with the procedure as described in Example 1.

Figure 3:
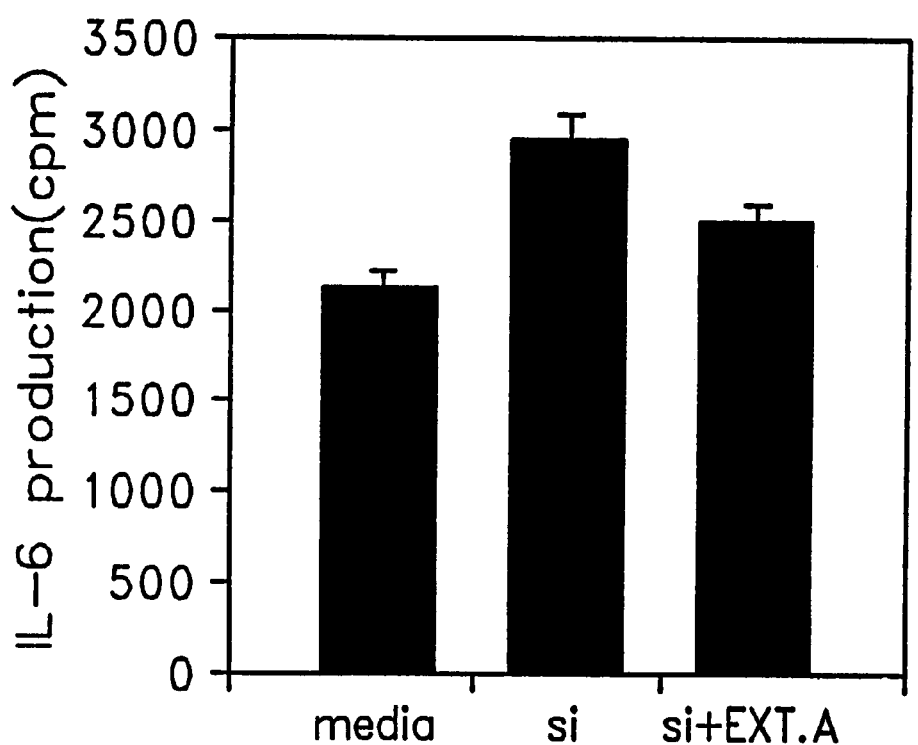
FIG. 3 represents the inhibitory effect of Extract A of *S. tetrandra* S. Moore on the production of IL-6 in rat alveolar macrophages.

As a result, it was observed that the production of IL-6 in rat alveolar macrophages was also inhibited by Extract A (FIG. 3). In FIG. 3, media, Si and Si+EXT. A represent non-treated control group, silica-stimulated sample and silica-stimulated and Extract A-treated sample, respectively.

EXAMPLE 3
Inhibition of IL-6 production by Extract C

In order to prepare experimental silicosis models, bronchia of Sprague-Dawley rats weighing about 150 g, each five rate per treating group, were opened and injected with 500 mg of silica dissolved in 0.5 ml of PBS.

After one week from the infection of silica, 40 mg of Extract C was administered orally, or 250 μg of mouse IL-6 antibody (MIL-6 Ab, Immunex, Seatle, U.S.A.) was injected intravenously or intraperitoneally, to the rats twice a week for 17 weeks. IL-6 activities in the serum (FIG. 4) and in the culture of pulmonary fibroblast obtained in Reference Example 1 (2) (FIG. 5) was determined according to the same procedures as described in Example 1.

Figure 4:
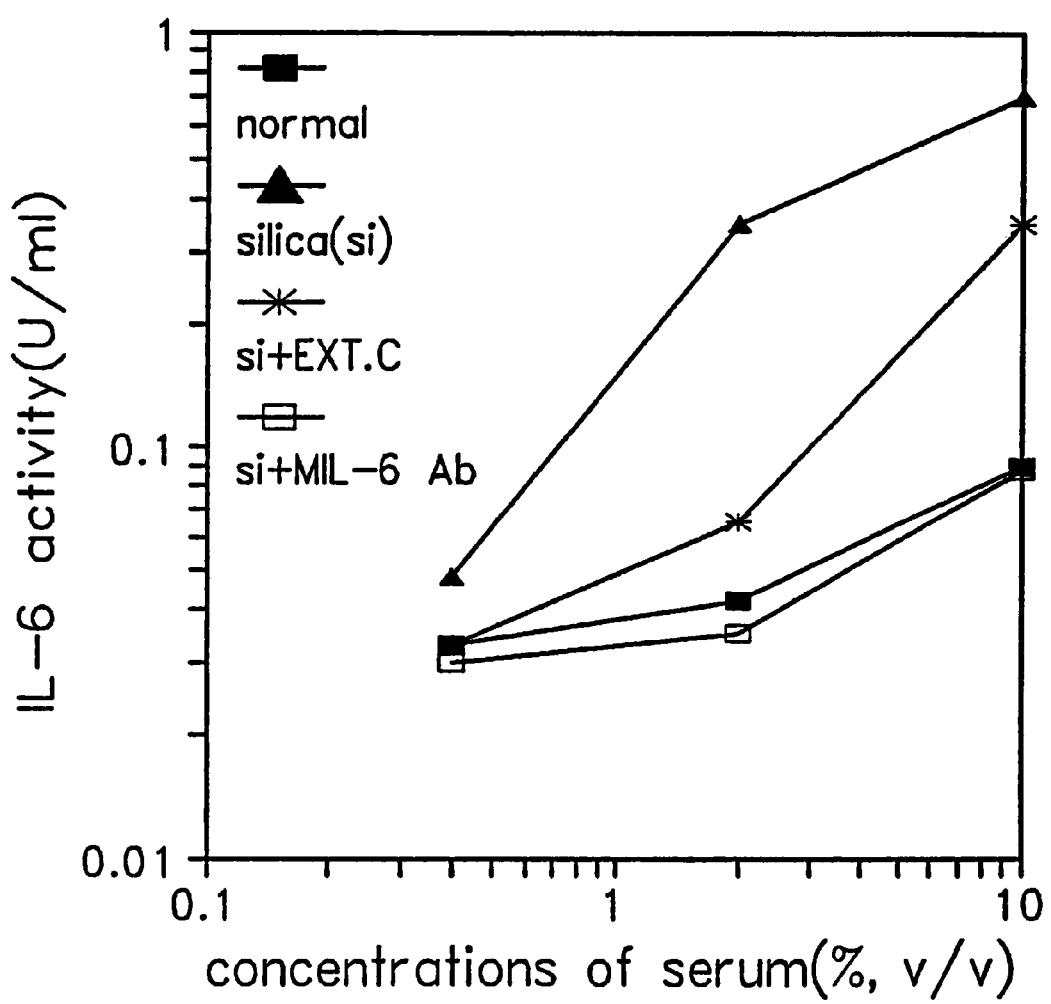
FIG. 4 discloses the inhibitory effect of Extract C of *S. tetrandra* S. Moore on the production of IL-6 in rats.
Figure 5:
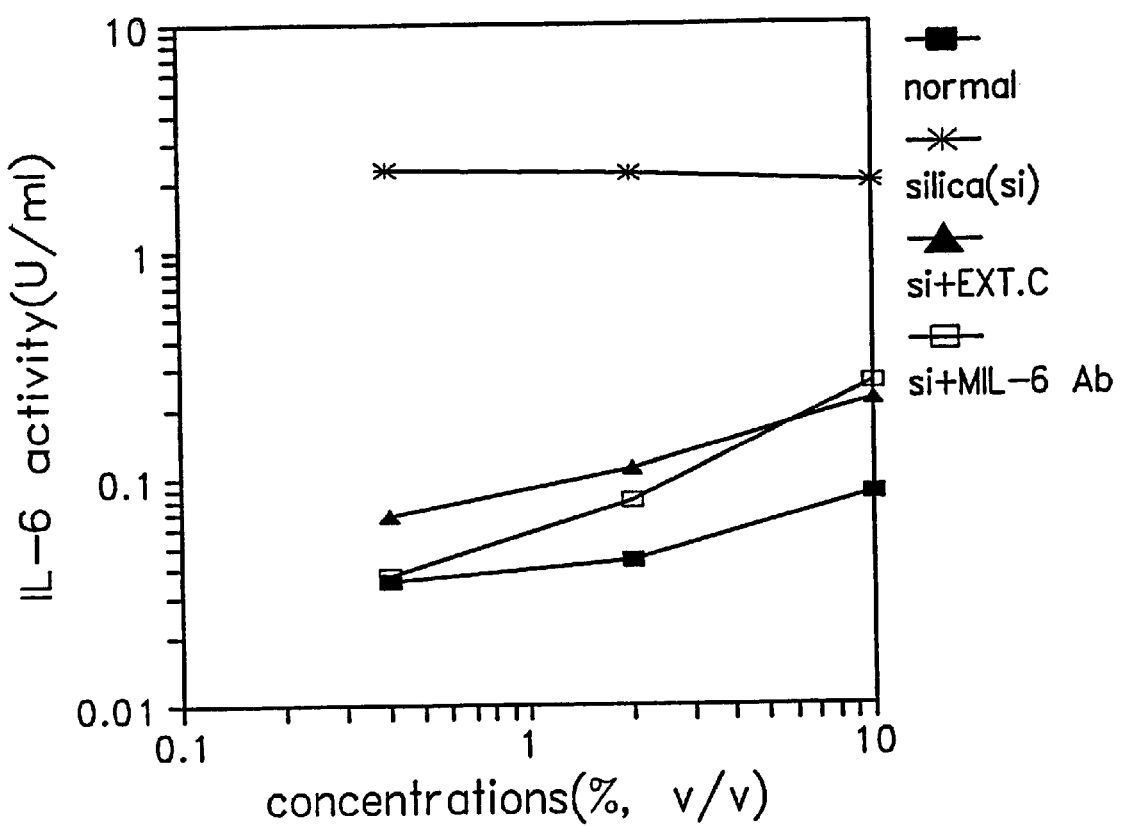
FIG. 5 presents the inhibitory effect of Extract C of *S. tetrandra* S. Moore on the production of IL-6 in rat pulmonary fibroblasts.

As can be seen from FIGS. 4 and 5, the activity of IL-6 was inhibited by Extract C in both cases, which shows that the extracts of *S. tetrandra* S. Moore exhibited their inhibitory effect on animal silicosis models. In FIGS. 4 and 5, normal, si, si+EXT.C and si+MIL-6 Ab represent PBS treated control group, silica-stimulated sample, silica-stimulated and Extract C-treated sample, and silica-stimulated and MIL-6 Ab-treated sample, respectively.

EXAMPLE 4

Repression of IL-6 Gene Expression by Extracts of *S. tetrandra* S. Moore

For the purpose of confirming that the extracts of *S. tetrandra* S. Moore repress the expression of IL-6 gene, the effect of said extracts on synoviocytes which is obtained from the patients of rheumatoid arthritis caused by the overproduction of IL-6(Hirano, T., et al., *Eur. J. Immunol.*, 18, 1797(1988)) was determined as follows.

The synoviocytes isolated in Reference Example 1 (3) were added to six wells of incubation plate in an amount of $1.5 \times 10^6$/well, and incubated at 37° C. under 5% $CO_2$ for 24 hours to be adhered to the wells. 1 µg/ml or 10 µg/ml of Extract B was added to the wells and the plate was incubated at 37° C. under 5% $CO_2$ for 3 days.

When the incubation was completed, the culture solution was centrifuged to remove the supernatant and the precipitated cells were washed with PBS and disrupted by adding 500 µl of denaturating solution (4M guanidinium thiocyanate, 25 mM sodium citrate, pH 7.0, 0.1M 2-mercapto-ethanol, 0.5% sarcosine) and pipetting gently. The resulting solution was transferred to a tube and 50 µl of 2M sodium citrate (pH 4.0) and 500 µl of water-saturated phenol were added thereto and mixed thoroughly. Then, 2-fold volume of chloroform was added to the mixture and the resulting mixture was stored on ice for 10 minutes and centrifuged at 12,000 rpm to obtain the supernatant. 1 ml of isopropyl alcohol was added to the supernatant and the resulting mixture was stored at –20° C. for 2 hours and then centrifuged at 12,000 rpm for 20 minutes to obtain the precipitated pellets. The pellets were washed with 70% methanol, dried and then dissolved in 20 µl of 0.1% diethyl pyrocarbonate-water to the final concentration of 10 µg/ml.

To synthesize a single strand cDNA from the RNA obtained as above, a reverse transcription reaction was carried out by employing M-MLV reverse transcriptase (Promega, U.S.A) as follows. To a reaction tube were added 5 µl of 5x reaction buffer(250 mM Tris-HCl, pH 8.3, 375 mM KCl, 15 mM $MgCl_2$, 50 mM dTT), 2 µl of 5 µM dNTP mixture (5 µM each of dATP, dCTP, dGTP and dTT), 1 µl (0.2 µg) of primer NotI-dT (5'-dCGCCGGCG(T)$_{18}$-3') (SEQ ID NO: 1), 1 µl of distilled water, 10 µl of said cellular RNA and 1 µl (200U) of M-MLV reverse transcriptase (Promega, U.S.A), and the resulting solution was mixed well, and then reacted at 42° C. for 30 minutes. The reaction was terminated by heating the solution at 90° C. for 5 minutes.

Using the above resulting solution, a polymerase chain reaction (PCR) was carried out to amplify cDNA.

20 µl of said resulting solution of reverse transcription reaction, 8 µl of 10x PCR buffer (100 mM Tris-HCl, pH 8.3, 400 nM KCl, 10 mM DTT, 15 mM $MgCl_2$, 5 µg/ml BSA), 1 µl (20 pmol) of 5'-end primer(5'-ATGAACTCCTTCTCC ACAAG-CGC-3') (SEQ ID NO: 2), 1 µl (20 pmol) of 3'-end primer(5'-GAAGAGCCCTCAGGCTGG-ACTG-3') (SEQ ID NO: 3), 69 µl of distilled water and 1 µl (2.5U) of Taq DNA polymerase (Promega, U.S.A.) were mixed well and the mixture was stored at 95° C. for 5 minutes to inhibit other undesired enzymes. The PCR was carried out by repeating 30 times the thermal cycle consisting of 95° C. for 1.5 minute; 55° C. for 1 minute; 72° C. for 1.5 minute, and the reaction mixture was consequently reacted at 95° C. for 1.5 minute; at 55° C. for 1 minute; and at 72° C. for 5 minutes.

Figure 6:
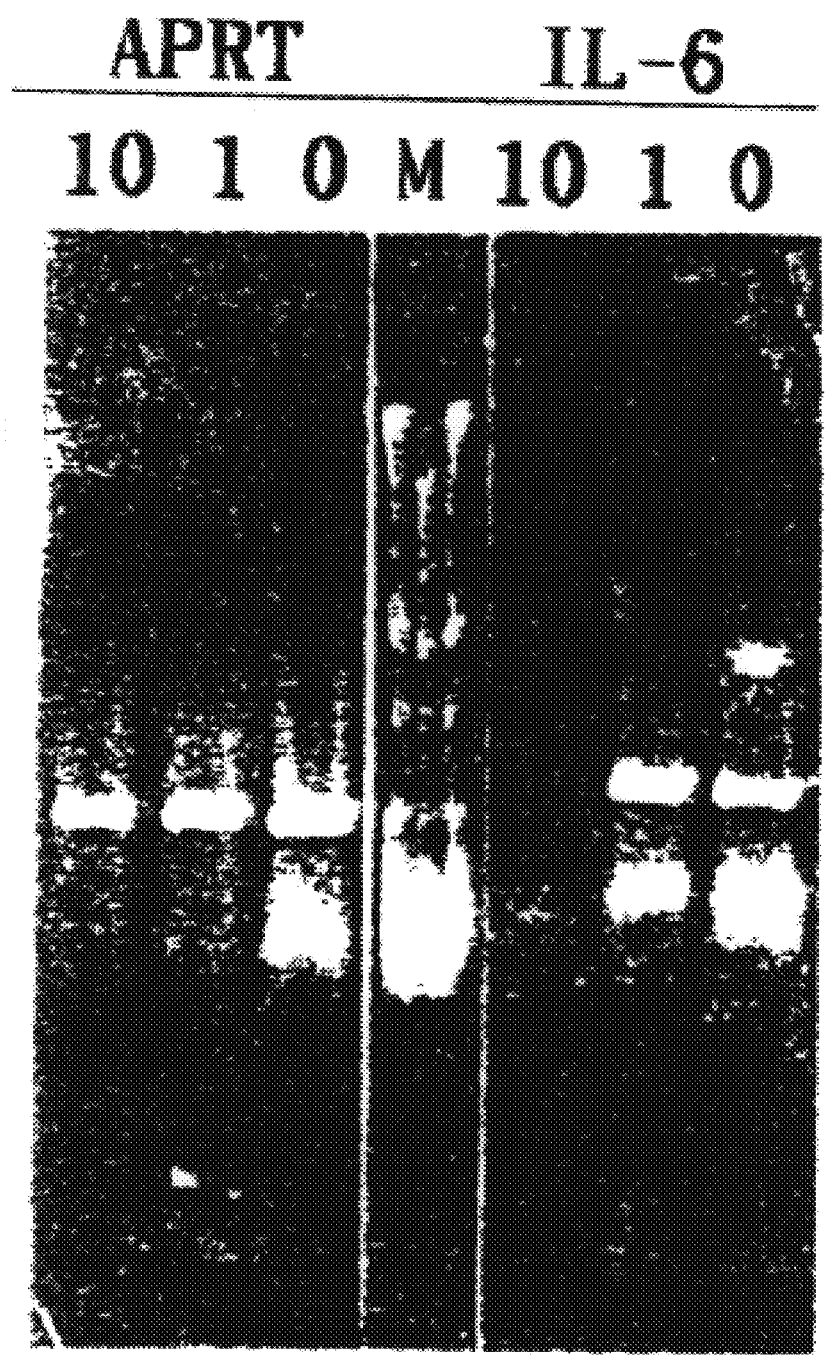
FIG. 6 illustrates the inhibitory effect of Extract B of *S. tetrandra* S. Moore on the IL-6 gene expression in synoviocytes of arthritis patients.

10 µl of the PCR product was subjected to an electrophoresis on 1.0% agarose gel at 100 volts for 30 minutes. The gel was stained in EtBr solution for 10 minutes, washed with distilled water and photographed (FIG. 6). As can be seen from FIG. 6, the expression of constantly expressed adenine phosphoribosyl transferase (APRT) RNA which was used as a control group was not influenced by Extract B, while that of IL-6 RNA was significantly repressed by 10 µg/ml of the Extract B. The result shows that the extracts of *S. tetrandra* S. Moore can repress the expression of IL-6 gene. In FIG. 6, lane M is a standard DNA size marker, and 10, 1 and 0 represent the concentration of Extract B in µg/ml.

EXAMPLE 5

Figure 7:
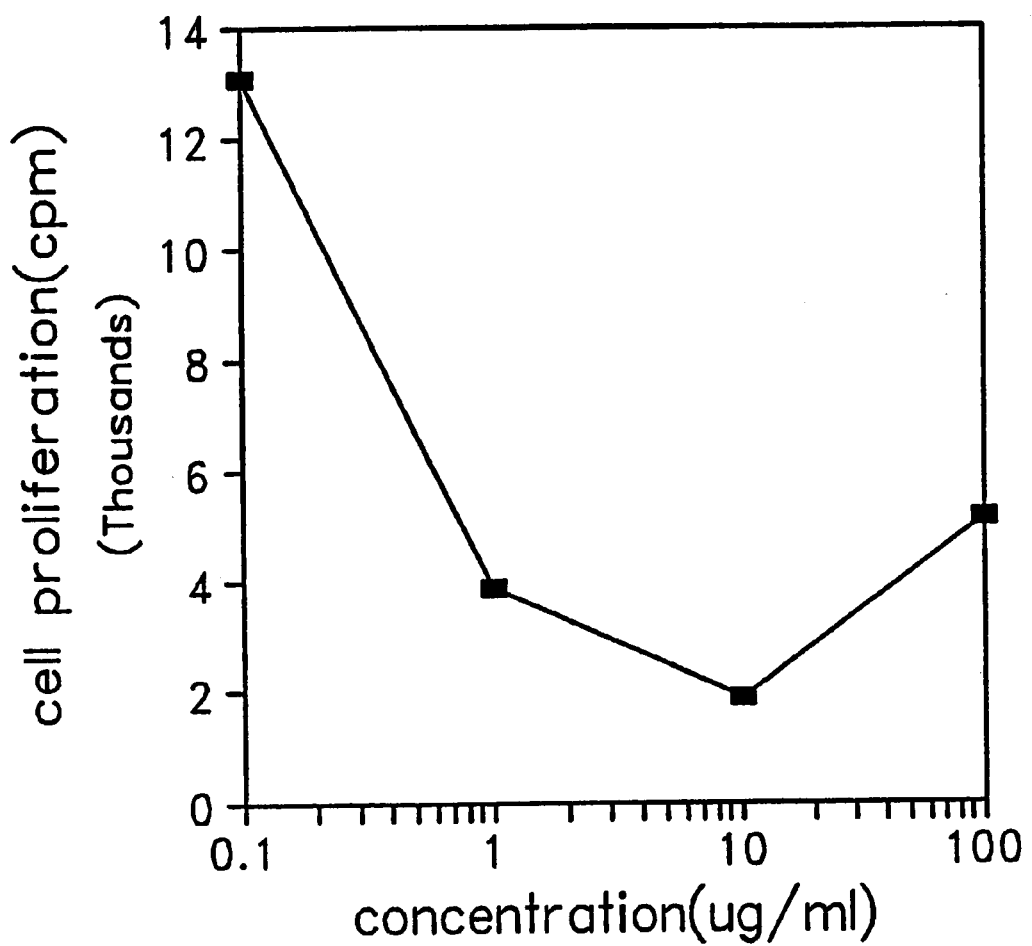
FIG. 7 displays the inhibitory effect of Extract A of *S. tetrandra* S. Moore on the synoviocyte proliferation in arthritis patients.

Inhibition of Proliferation of Synoviocytes by Extracts of *S. tetrandra* S. Moore Human monocyte/macrophage was treated with Extract A in a concentration ranging from 0.1 to 100 µg/ml and cultured according to the procedure as described in Reference Example 1 (4). The culture was dialyzed against PBS, and the dialyzate was added to $1 \times 10^4$ cells of synoviocyte, and then the cells were cultured for 5 days. After the addition of $^3$H-thymidine to the culture, the cells were cultured for additional 4 hours and the amount of 3H-thymidine incorporated in the cell was determined by employing liquid scintillation counter (FIG. 7). As can be seen from FIG. 7, Extract A inhibited the proliferation of synoviocyte significantly in a concentration of 10 µg/ml.

EXAMPLE 6

Inhibition of Collagen Synthesis by Extracts of *S. tetrandra* S. Moore

IL-6 is known as a cytokine which causes fibrogenesis and induces collagen synthesis in rat fibroblasts (Kang, H. S., et al., *Korean. J. Immunol.*, 14, 193(1992)). For the purpose of confirming the ability of extracts of *S. tetrandra* S. Moore to suppress such action of IL-6, their inhibitory effect on the collagen synthesis in rat pulmonary fibroblasts and pulmonary tissues was determined. The amount of produced collagen in the culture of rat pulmonary fibroblasts was measured by an indirect ELISA method, and that in the culture of pulmonary tissue was determined by measuring the concentration of hydroxyproline and calculating the amount of collagen therefrom by using the standard curve of internal control group.

To measure the amount of synthesized collagen in the culture of rat pulmonary fibroblasts, collagen(Sigma, type I) as an internal control group was dissolved thoroughly in 1M acetic acid containing 1 mg/ml of pepsin, and the solution was serially diluted by 5-fold with coating buffer (0.05M carbonate, pH 9.6) in a concentration ranging from 1 µg to 16 pg. The diluted solutions were added to the wells of flat-bottomed microtiter plate (Dynatech, Cantilly, Va., U.S.A., Immulon 2) in an amount of 100 µl/well.

On the other hand, 1 ml of the culture supernatants of rat pulmonary fibroblast obtained in Reference Example 1 (2) was 10 to 20-fold concentrated by using speed vac dryer (Savant, Hicksville, N.Y., U.S.A.) and dissolved in 100 µl of coating buffer (0.1M $NaHCO_3$, 0.02% $NaN_3$; pH was adjusted to 9.6 with $Na_2CO_3$) and the solution was added to the wells in an amount of 100 µl/well and then coated at 4° C. overnight.

The plate was washed three times with washing buffer (PBS, 0.05% Tween 20, pH 7.4), and it bovine serum albumin (BSA, Sigma) was added to the wells in an amount of 100 μl/well. The plate was incubated at a room temperature for 2 hours to block the uncoated parts. The plate was washed four times with the same buffer as above, and alkaline phosphatase-conjugated rabbit anti-goat IgG (Cappel, Dunham, N.C., U.S.A.) which was 1,000-fold diluted with a dilution buffer (0.05M Tris-HCl M $MgCl_2.6H_2O$, 0.15M NaCl, 0.02% $NaN_3$, 1% BSA, 0.05% Tween 20, pH 8.1) was added to the wells in an amount of 100 μl/well.

Figure 8:
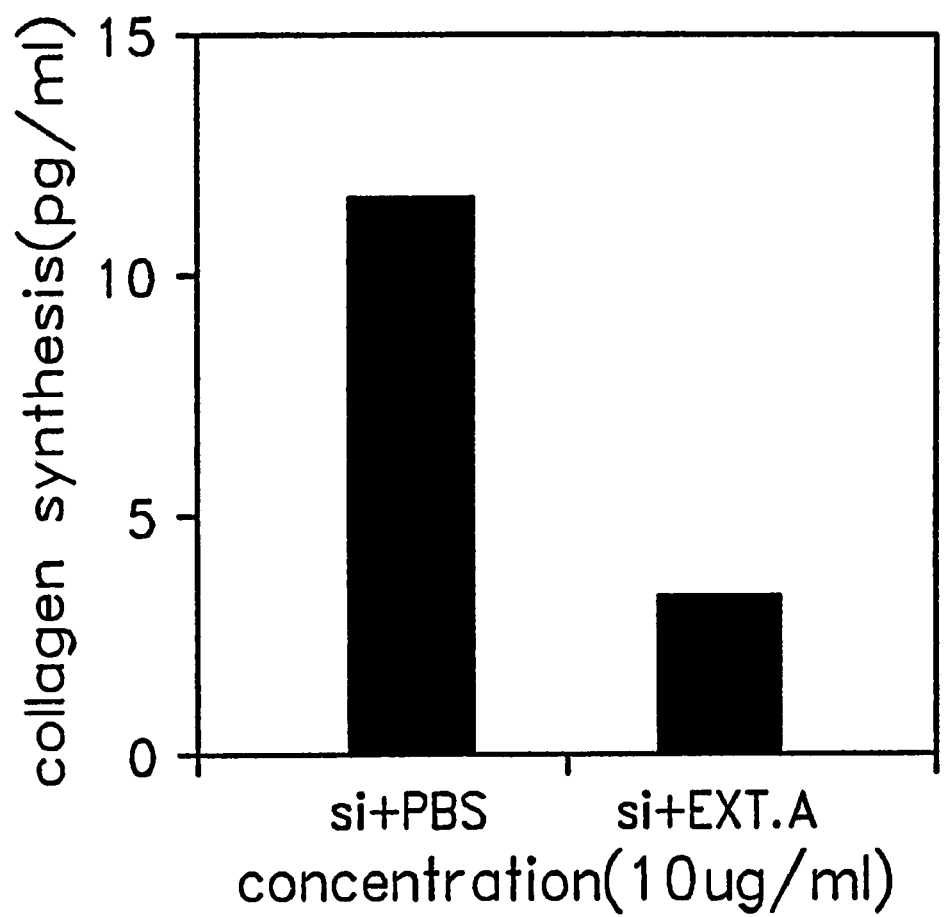
FIG. 8 exemplifies the inhibitory effect of Extract A of *S. tetrandra* S. Moore on the production of collagen in rat pulmonary fibroblasts.

The plate was incubated at 37° C. for 2 hours and then washed three times with the same buffer as above. To the wells was added 100 μl/well of p-nitrophenyl phosphate which was diluted with substrate buffer (0.05M $NaHCO_3$, 10 mM $MgCl_2.6H2O$, pH 9.8) in a concentration of 1 mg/ml, and the O.D. of the culture was determined by using an ELISA reader at 405 nm. The amount of produced collagen was calculated from the O.D. value with reference to that of the internal control group. As a result, it was observed that the amount of synthesized collagen was significantly decreased in the culture of rat pulmonary fibroblasts which were pretreated with 10 μl/ml of Extract A at 37° C. for an hour and treated with 100 μl/ml of silica for 48 hours (FIG. 8). In FIG. 8, si+PBS and si+EXT.A represent silica-stimulated sample and Extract A-treated and silica-stimulated sample, respectively.

Further, for the purpose of determining the amount of synthesized collagen in rat pulmonary tissues in accordance with the procedures of Example 3, bronchia of rats were opened and injected with 500 mg of silica, and 40 mg of Extract C dissolved in 1% DMSO or only 1% DMSO were administered orally to the rate twice a week for 17 weeks, and then the amount of hydroxyproline was measured as follows.

0.1 to 0.2 g of the rat pulmonary tissue was mixed with 1 ml of PBS and then crushed in a Pyrex tube (Corning, Rochester, N.Y., U.S.A.). The resulting tissue extract was ruptured by using an ultrasonicator (Heat system, W-380), 1 ml of hydrochronic acid was added thereto and the mixture was dried overnight at 120° C. in a drying oven. The resultant was freezed in a freezer, lyophilized in a freeze-dryer (Labconco) and dissolved completely by adding 1 ml of distilled water thereto. 50 μl of the resulting solution was added to a microcentrifuge tube and the solution was diluted by adding 50 μl of distilled water thereto. As an internal control group, trans-γ-hydroxy-L-proline(Sigma) was diluted in a concentration ranging from 20 μg to 150 pg, and 100 μl of each diluted solutions was added to the microcentrifuge tube.

0.9 ml of a solution prepared by dissolving 1.41 g of chloramine-T(sodium N-chloro-P-toluene sulfonamide) in 10 ml of n-propanol and 10 ml of distilled water was added to the tube, which was stored at a room temperature for 20 minutes. Then, to the resulting mixture was added 1 ml of aldehyde/perchloric acid solution prepared by dissolving 15 g of p-dimethyl aminobenzaldehyde in 62 ml of n-propanol and then adding 26 ml of 60% perchloric acid thereto to make the total volume of 100 ml, and the resultant was mixed well. The microcentrifuge tube was put into 65° C. water bath for 15 minutes to develop colors, O.D. of the sample was measured at 650 nm, and the amount of hydroxyproline in the sample was calculated by employing the standard curve of internal control group.

Figure 9:
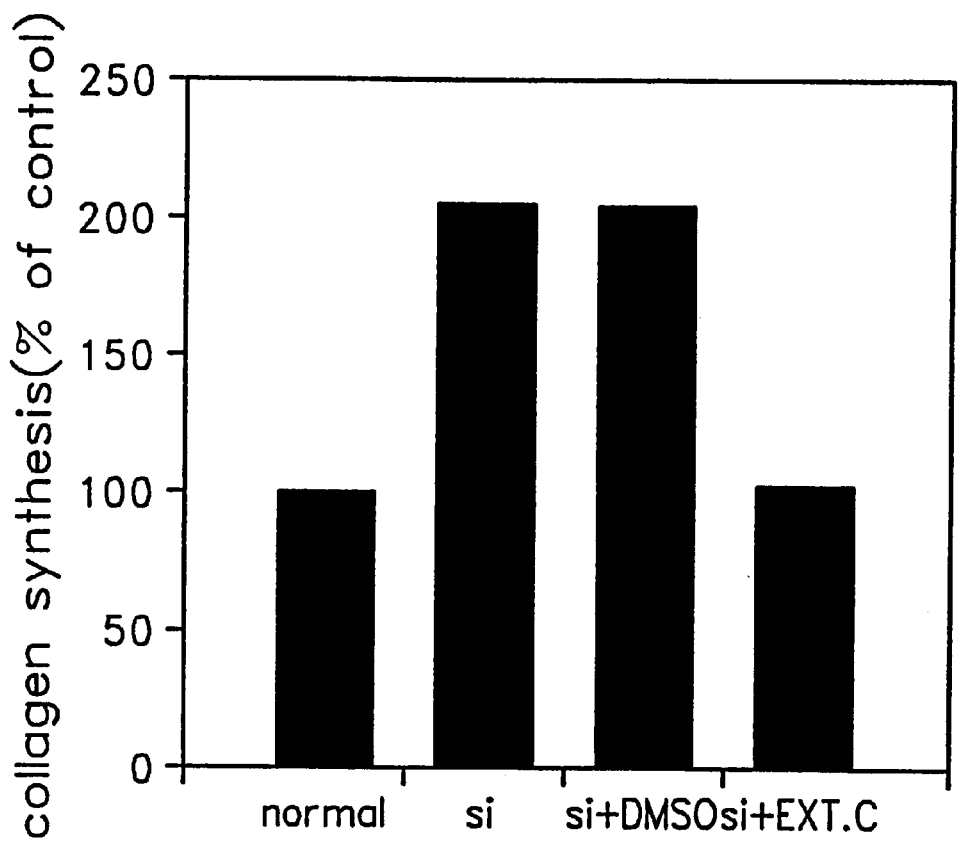
FIG. 9 provides the inhibitory effect of Extract C of *S. tetrandra* S. Moore on the production of collagen in rat pulmonary tissues.

As can be seen from the result in FIG. 9, when the amount of collagen produced in normal rat pulmonary tissue (normal) is regarded as 100%, the amount of collagen synthesized in rat pulmonary tissue treated with silica only (si) or treated with silica and dimethylsulfoxide (si+DMSO) was remarkably high, while the amount of synthesized collagen was decreased by 50% in rat pulmonary tissue treated with silica, DMSO and Extract C(si+EXT.C). The above result shows that the extracts of S. tetrandra S. Moore have anti-fibrogenic activity.

EXAMPLE 7

Inhibition of Production of Reactive Oxygen Species by Extracts of S. tetrandra S. Moore Inflammatory responses are known as a cascade reaction comprising the secretion of various cytokines, e.g., IL-6, from immune cells stimulated by various stimulants; production of phospholipase $A_2$, lysosomal enzyme, reactive oxygen species, etc. by other immune cells stimulated by said cytokines; and damage of tissues induced by the above products(Pruzanski, W. and Vadas, P., Immunol. Today, 12, 143(1991)). The ability of the extracts of S. tetrandra S. Moore to block the inflammatory reactions was tested by measuring their inhibitory activity to the production of reactive oxygen species, e.g., $H_2O_2$ and $O_2^-$.

The amount of $H_2O_2$ was determined by a microassay employing 96-well microplate as follows. $5 \times 10^5$ cells of neutrophils were added to each well containing RPMI 1640 medium, and 25 μl of horseradish peroxidase (500 μg/ml; type II, Sigma) and 75 μl of phenol red(1 mg/ml) were added to each of the wells. Thereafter, the cells were treated with 10, 20 and 50 μg/ml of Extract A for an hour, stimulated with $10^{-7}$M phorbol myristate acetate (PMA) and then reacted at 37° C. for 60 minutes. When the incubation was completed, 3M NaOH was added to the wells in an amount of 25 μl/well to stop the reaction and O.D. was measured at 620 nm by using ELTSA reader (Dynatech Lab. Inc.) to determine the change of colors with respect to the oxidation of phenol. The amount of $H_2O_2$ was determined by employing a standard curve prepared by diluted $H_2O_2$ (Sigma).

For the purpose of measuring the amount of produced $O_2^-$, neutrophils suspended in RPMI 1640 medium in a concentration of $1 \times 10^6$ cells/800 μl was added to a part of the wells of 24-well plate and 10 μg/ml of superoxide dismutase (SOD, Sigma) was added to the empty wells. The plate was stored at 37° C. for 2 minutes, and cytochrome C(3 mg/ml, Sigma) was added to the wells in a concentration of 100 μl/well. The cells were treated with 10, 20 and 50 μg/ml of Extract A for an hour and reacted at 37° C. for 20 minutes by introducing $10^{-7}$M PMA as a stimulant. The reaction was terminated by adding 1 mM N-ethylmaleimide (Sigma) to the wells and the culture was centrifuged at 1,600 xg for 10 minutes to obtain a supernatant. The change of color of the supernatant caused by the reduction of cytochrome C was measured at 550 nm by using a UV-Visible spectrophotometer (Kontron Instrument, Milano, Italy). The amount of produced $O_2^-$ was represented by the concentration of SOD which can suppress the reduction of cytochrome C in $1 \times 10^6$ cells for 20 minutes, by employing the extinction coefficient of cytochrome C($E_{550nm}=1.38 \times 10^4$ $mM^{-1}cm^{-1}$). As can be seen from Table I, 50 μg/ml of Extract A inhibits the production of $H_2O_2$ by 50%, and the production of $O_2^-$ by 25%. The result shows that Extract A has a strong inhibitory activity to the inflammatory response.

TABLE I

Inhibitory effect of Extract A of *S. tetrandra* S. Moore
on the production of reactive oxygen species in human neutrophils

| Sample | Amount of produced reactive oxygen species(% to the control group) | |
|---|---|---|
|  | $H_2O_2$(nM/60 min.) | $O_2^-$(nM/20 min.) |
| Medium only | 11.5(11.1) | 2.0(12.9) |
| PMA | 103.6(100) | 15.5(100) |
| PMA + Extract A |  |  |
| 10 μg/ml | 90.6(87.4) | 12.7(81.9) |
| 20 μg/ml | 58.6(56.6) | 12.4(80.0) |
| 50 μg/ml | 50.6(48.8) | 11.5(74.2) |

Figure 10:
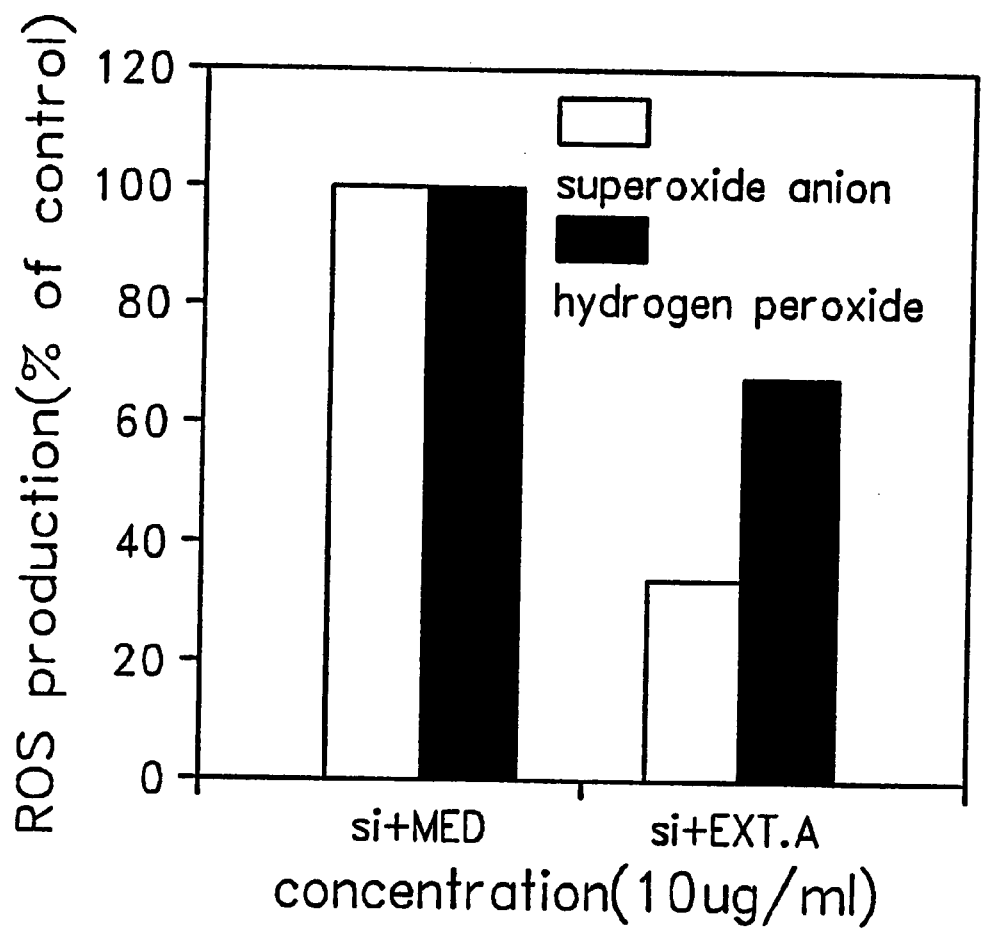
FIG. 10 demonstrates the inhibitory effect of Extract A of *S. tetrandra* S. Moore on the production of the reactive oxygen species in human monocytes and macrophages.

On the other hand, the same procedures as above were repeated to determine the amount of $H_2O_2$ and $O_2^-$ produced by $5 \times 10^5$ cells of human monocytes/macrophage which was treated with 10 μg/ml of Extract A at 37° C. for an hour and then stimulated by 100 μg/ml of silica. As can be seen from FIG. 10, the amounts of $H_2O_2$ and $O_2^-$ decreased significantly in the silica-stimulated and Extract A-treated monocytes/macrophage (si+EXT.A) in contrast with the control group treated with only silica(si+MED).

EXAMPLE 8
Inhibition of Hepatocirrhosis by Extracts of *S. tetrandra* S. Moore Hepatocirrhosia(hepatic sclerosis) is characterized by the fibrogenesis of the whole liver, complete disruption of liver parenchyma by the fibrous septa, and formation of regenerative nodules. It is derived mostly from a chronic hepatitis or chronic alcoholism, however, the precise causes thereof are unknown. In a hepatocirrhosis patient, the amount of cytokines, e.g., IL-6 which is involved in the inflammation and fibrogenesis, is in an increased state; and, therefore, the inhibition of hepatocirrhoeis by the extracts of *S. tetrandra* S. Moore may be determined by the inhibitory activity to IL-6.

Figure 11A:
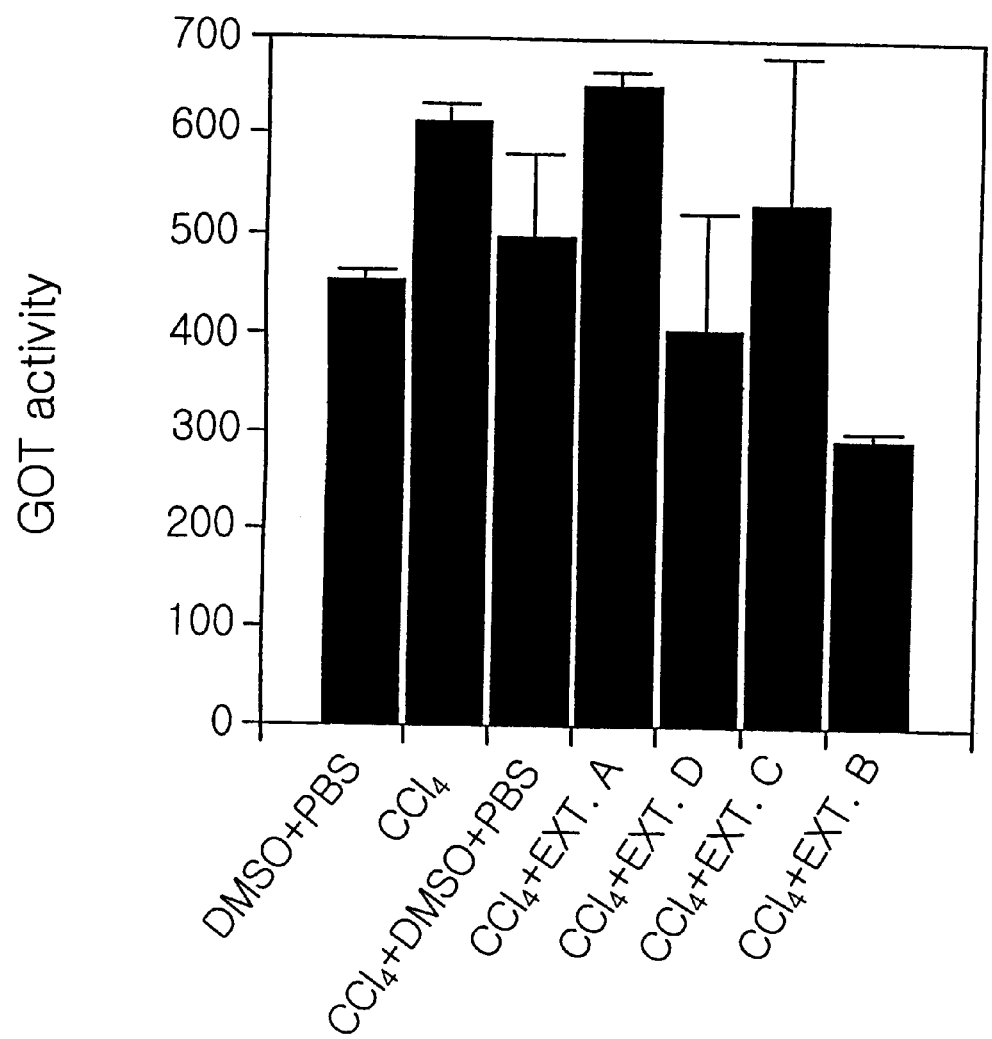
FIGS. 11A and 11B disclose the effect of Extracts A, B, C and D of *S. tetrandra* S. Moore on GOT and GPT levels in serum of a rat suffered from induced hepatocirrhosis respectively.
Figure 11B:
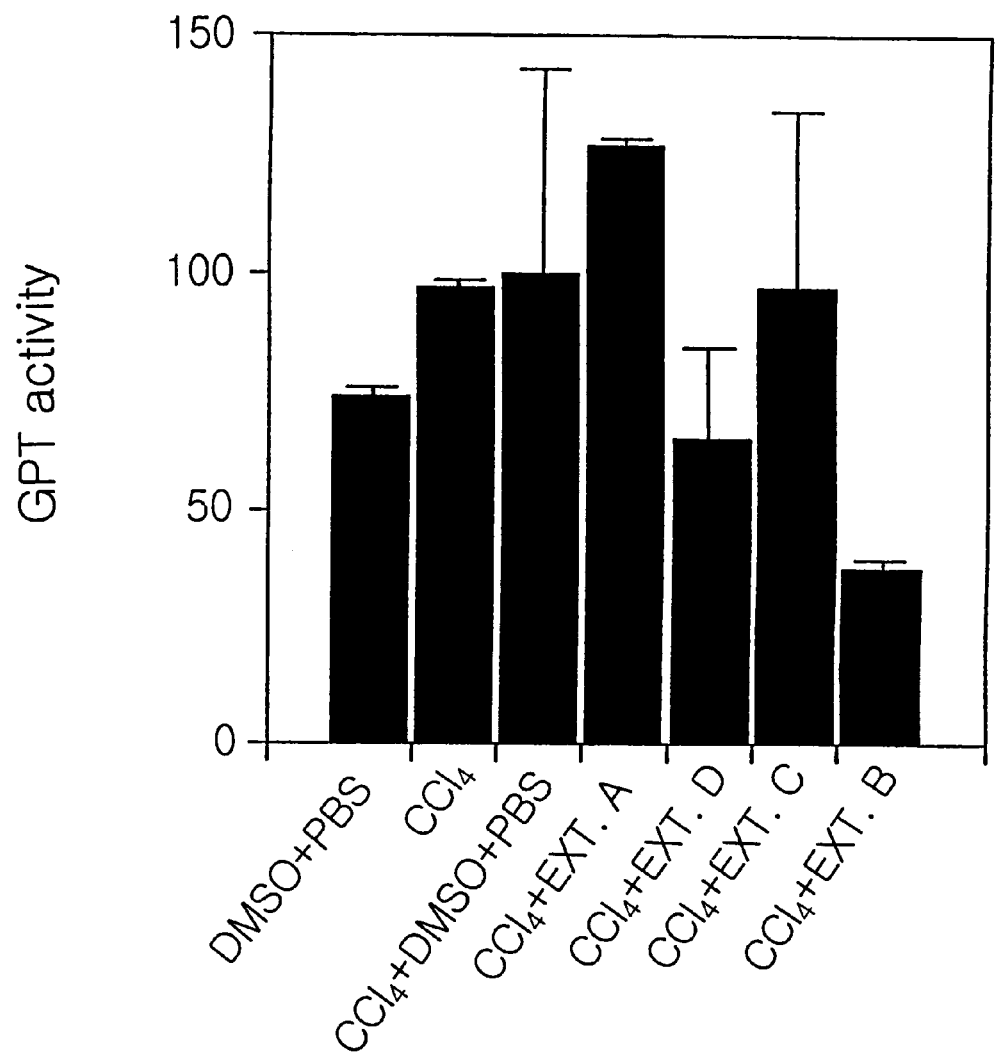

To induce the experimental hepatocirrhosis in 4-week aged male Sprague-Dawley rate(Nakataukasa, H., et al., *J. Clin. Invest.*, 85, 1833–1843(1990)), 1.0 ml/100 g of body weight of $CCl_4$ solution(50% $CCl_4$+50% corn oil) was injected intraperitoneally to the rate twice a week, and 0.2 ml each of Extract A, B, C or D was administered orally at the time of the injection of $CCl_4$ twice a week. After 13 weeks from the start of the test, each of the rats was anesthetized with ether and the blood samples were obtained from the heart to determine serum glutamic-oxaloacetic transaminase (sGOT) value and serum glutamic-pyruvic traneaminase (sGPT) value (FIGS. 11A and 11B).

As can be seen from FIG. 11, when compared with the blood sample obtained from the rat treated with $CCl_4$, DMSO and PBS which was used as a control group, sGOT values of the blood samples obtained from the rate treated with Extract A or C were not decreased, but those of samples obtained from the rat treated with Extract D or B decreased by 20% and 40%, respectively. Further, sGPT in the blood samples obtained from the rate treated with Extract B was decreased more than 60%.

For the pathohistological examination of the livers separated from the above rats, the liver was fixed in 10% aqueous solution of neutral formalin, spread out in 4 mm thickness and then embedded in paraffin. The embedded tissue was sectioned in 5 mm thickness, stained with hematoxylin eosin and Masson's trichrome, and then observed under a microscope (FIGS. 12A and 12F).

Figure 12A:
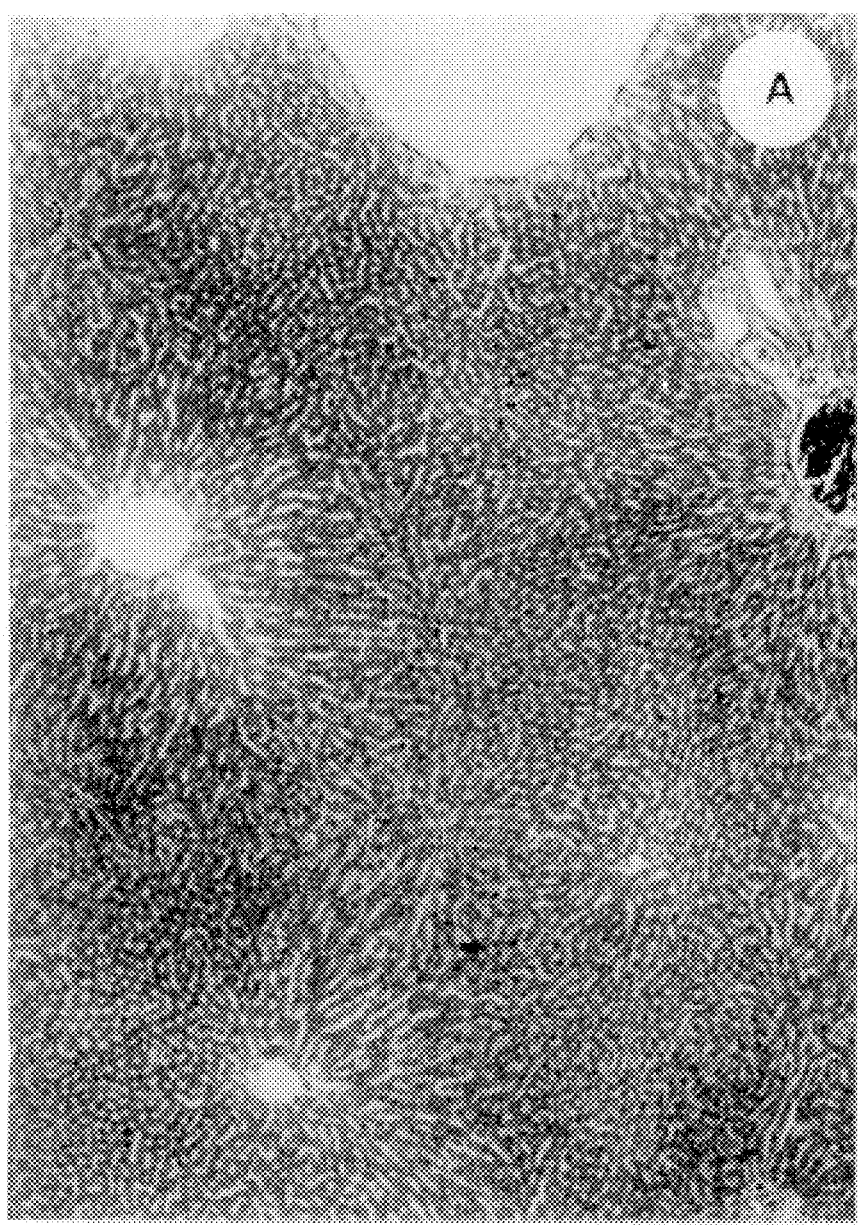
FIGS. 12A to 12F show the sectional views of the livers of a normal rat and the rats administered with $CCl_4$ only, $CCl_4$ plus Extract A, $CCl_4$ plus Extract D, $CCl_4$ plus Extract C, and $CCl_4$ plus Extract B, respectively.
Figure 12B:
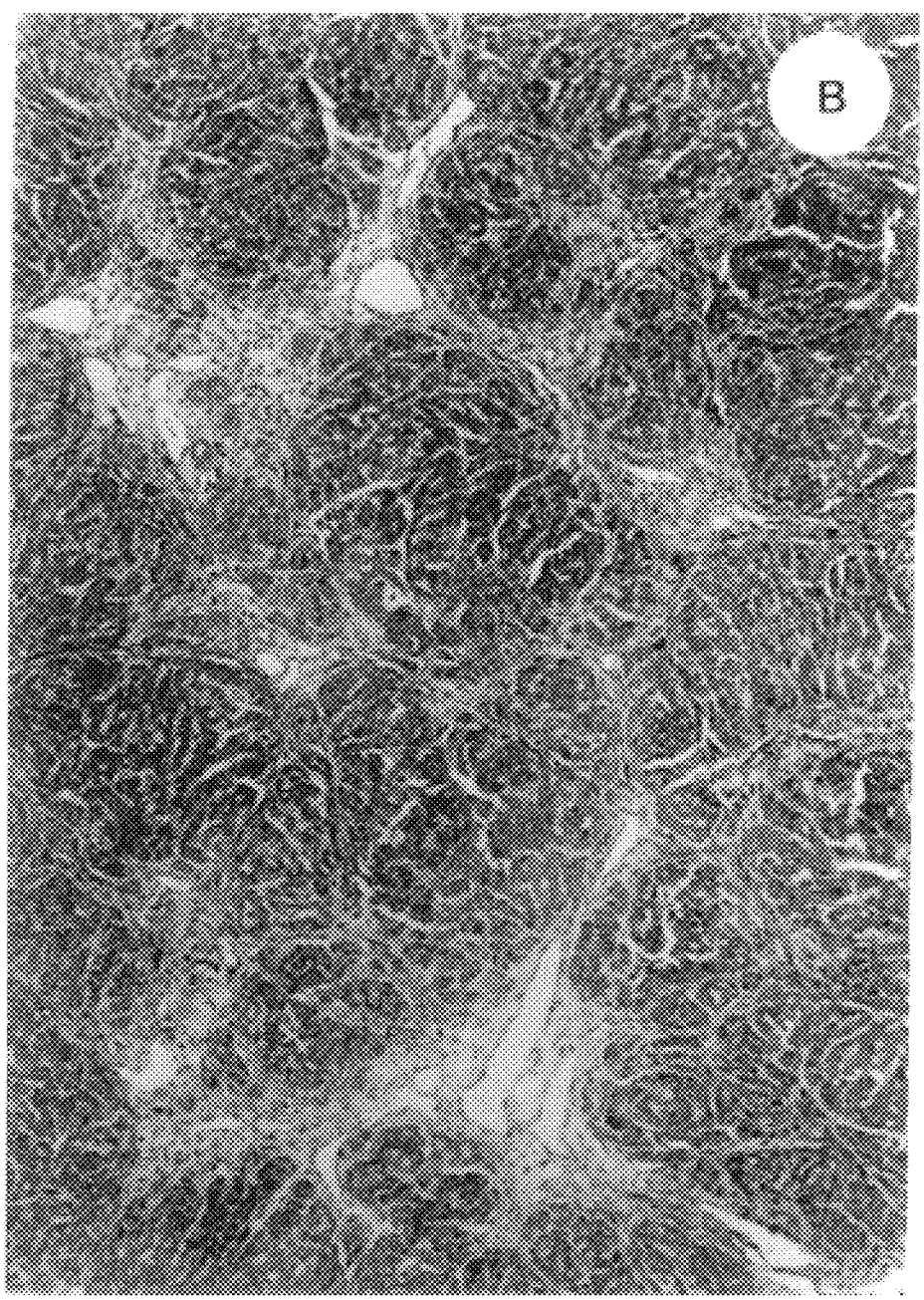
Figure 12C:
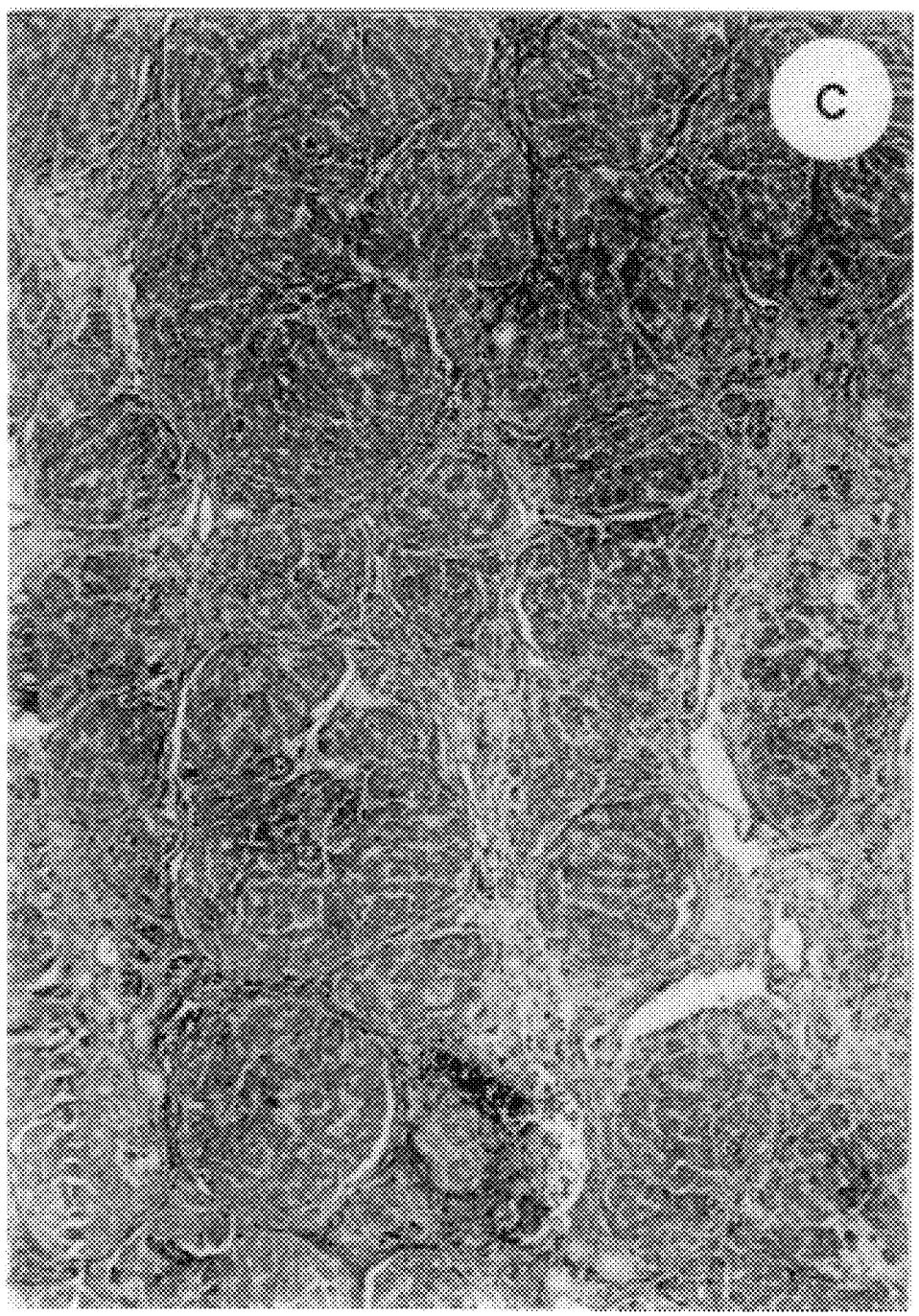
Figure 12D:
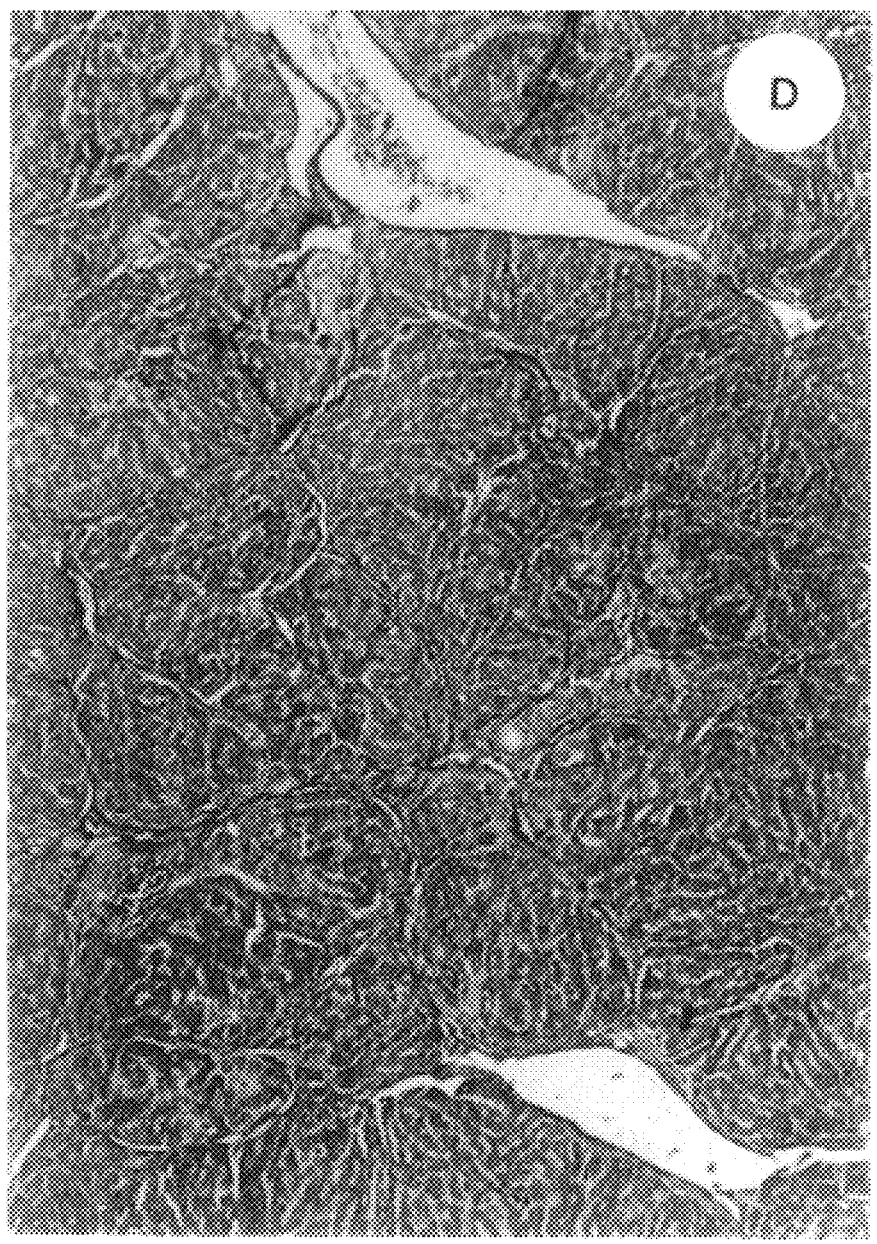
Figure 12E:
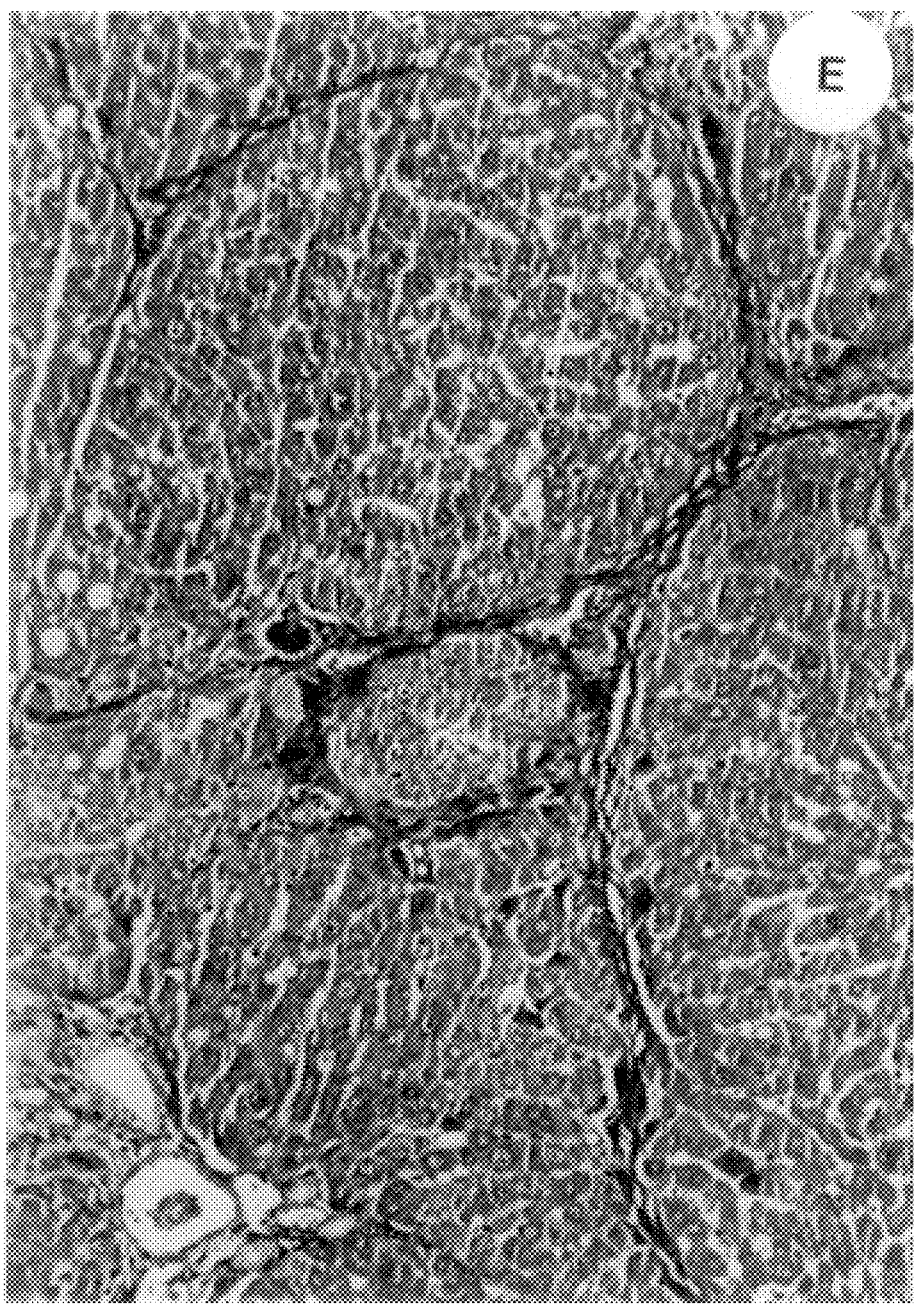
Figure 12F:
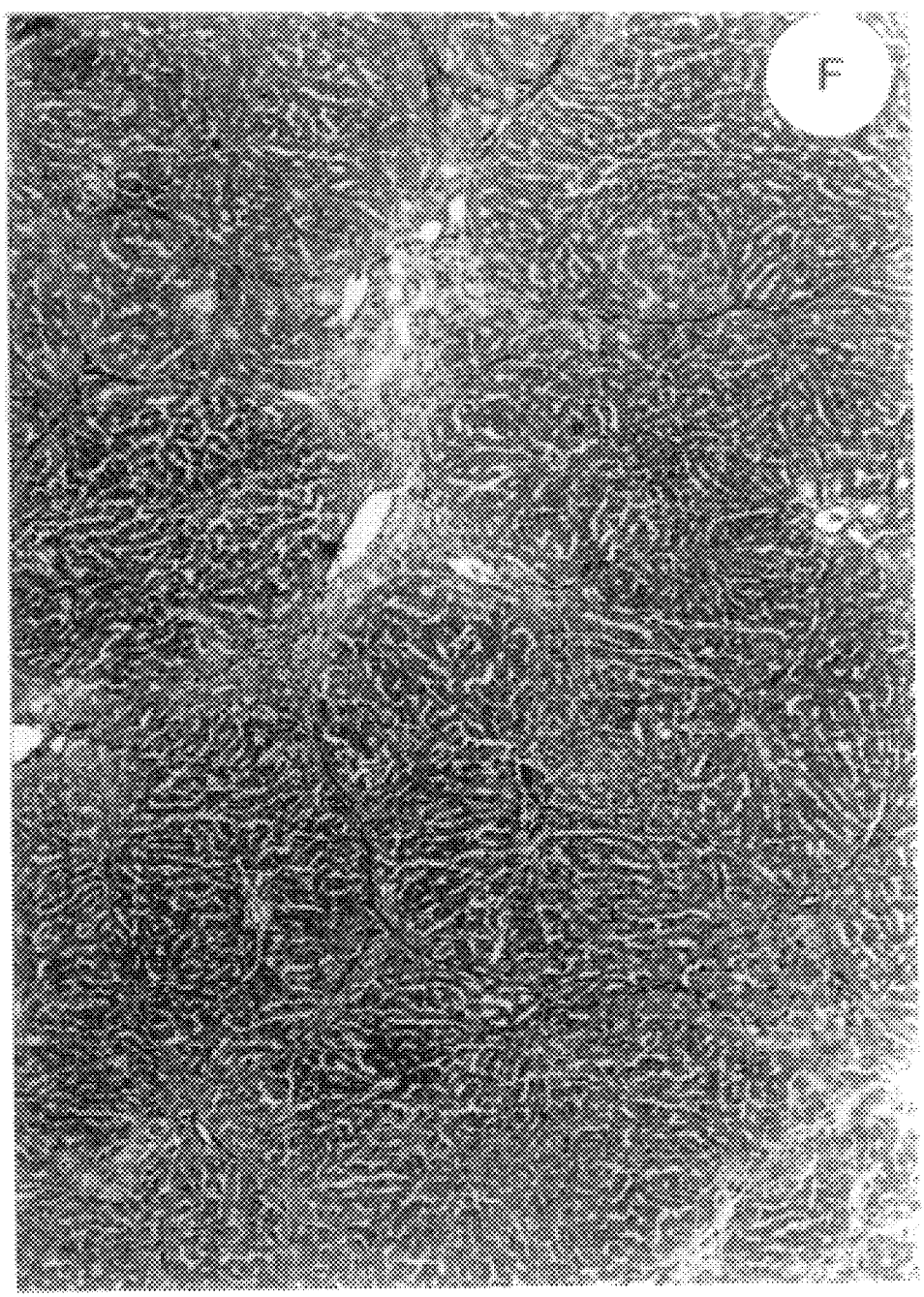

As can be seen from FIG. 12, in the liver of the rat administered with $CCl_4$ only (FIG. 12B), the nodule formation of hepatic lobules with the thickened fibrous bands was remarkable compared with the normal liver (FIG. 12A). In the livers of the rats administered with $CCl_4$ and Extract B (FIG. 12F); $CCl_4$ and Extract C (FIG. 12E); and $CCl_4$ and Extract D (FIG. 12D), even though signs of hepatocirrhosis were shown, their fibrous bands surrounding the nodule of hepatic lobule were thinner than those of the liver obtained from the rat treated with $CCl_4$ only, many nodules were incomplete, and the regenerative change of hepatic cells decreased compared with that of the liver obtained from the rat treated with $CCl_4$ only. In the liver of the rate administered with $CCl_4$ and Extract A (FIG. 12C), the inhibitory effect on the hepatocirrhosis was lower than those of FIGS. 12D, 12E and 12F.

The following Formulation Example is for illustration only and not intended to limit the scope of the invention in any way.

Formulation Example

Hard gelatin capsules were prepared using the following ingredients:

|  | Quantity (mg/capsule) |
|---|---|
| Active ingredient | 20 |
| Starch, dried | 160 |
| Magnesium stearate | 20 |
| Total | 200 mg |

The above ingredients were mixed and filled into hard gelatin capsules in 200 mg unit quantities.

While the invention has been described with respect to the above specific embodiments, it should be recognized that various modifications and changes may be made and also fall within the scope of the invention as defined by the claims that follow.

What is claimed is:

1. A method for treating hepatocirrhosis, which comprises administering an extract from the root of *Stephania tetrandra* S. Moore to a patient suffering from hepatocirrhosis in an amount effective to inhibit the production of interleukin-6.

* * * * *